(12) United States Patent
Abdelgawad

(10) Patent No.: US 11,759,240 B2
(45) Date of Patent: Sep. 19, 2023

(54) ADAPTIVE TIBIOTALOCALCANEAL ARTHRODESIS NAIL—NAIL, ADAPTER SYSTEM

(71) Applicant: Amr Abdelgawad, Brooklyn, NY (US)

(72) Inventor: Amr Abdelgawad, Brooklyn, NY (US)

( * ) Notice: Subject to any disclaimer, the term of this patent is extended or adjusted under 35 U.S.C. 154(b) by 0 days.

(21) Appl. No.: 17/302,833

(22) Filed: May 13, 2021

(65) Prior Publication Data
US 2021/0307794 A1 Oct. 7, 2021

Related U.S. Application Data

(60) Provisional application No. 63/003,638, filed on Apr. 1, 2020.

(51) Int. Cl.
*A61B 17/72* (2006.01)
*A61B 17/00* (2006.01)
*A61B 17/17* (2006.01)

(52) U.S. Cl.
CPC ........ *A61B 17/7291* (2013.01); *A61B 17/725* (2013.01); *A61B 17/1717* (2013.01); *A61B 2017/00486* (2013.01)

(58) Field of Classification Search
CPC .............. A61B 17/7291; A61B 17/725; A61B 2017/00486; A61B 17/1717
USPC ...................................................... 606/62–68
See application file for complete search history.

(56) References Cited

U.S. PATENT DOCUMENTS

| | | | | |
|---|---|---|---|---|
| 5,472,444 A | * | 12/1995 | Huebner | A61B 17/72 606/62 |
| 2009/0157077 A1 | * | 6/2009 | Larsen | A61B 17/1782 606/62 |
| 2013/0325006 A1 | * | 12/2013 | Michelinie | A61B 17/1725 606/62 |
| 2017/0056077 A1 | * | 3/2017 | Fallin | A61B 17/7291 |

\* cited by examiner

*Primary Examiner* — Eduardo C Robert
*Assistant Examiner* — Tara Rose E Carter
(74) *Attorney, Agent, or Firm* — Dunlap Bennett & Ludwig, PLLC; Anna L. Kinney

(57) ABSTRACT

An arthrodesis nail and nail adapter system having multiple coupling positions includes a bent arthrodesis nail and a nail adapter. The nail has multiple evenly spaced notches. The nail adapter has multiple evenly spaced protrusions corresponding to the notches. An arthrodesis nail adapter and target arm system having multiple coupling positions includes a nail adapter and a target arm. The nail adapter has a predetermined coupling orientation with a bent arthrodesis nail. The target arm has multiple coupling positions with the nail adapter. The arthrodesis nail and nail adapter system allows rotation of the bent nail for reduction of ankle deformity.

10 Claims, 3 Drawing Sheets

ADAPTIVE TIBIOTALOCALCANEAL ARTHRODESIS NAIL—NAIL, ADAPTER SYSTEM

CROSS-REFERENCE TO RELATED APPLICATION

This application claims the benefit of priority of U.S. provisional application No. 63/003,638, filed Apr. 1, 2020, the contents of which are herein incorporated by reference.

BACKGROUND OF THE INVENTION

The present invention relates to a tibiotalocalcaneal nail for arthrodesis and, more particularly, to an adaptive nail and nail adapter system that has a plurality of effective interfaces.

The currently commercially available tibiotalocalcaneal (TTC) nail (with its connection to a nail adapter) is either straight or bent in valgus (outwards). The nail cannot be rotated in the ankle, it can only be applied in one position (valgus position). As shown in prior art FIGS. 6 and 7, all currently available TTC nails 30 have three slots or notches 36 that will align with three prongs or protrusions 34 in the adapter 32 or vice versa. The slots 36 and prongs 34 have a placement such that the nail and the nail adapter can only be coupled in a single predetermined coupling orientation. In cases of ankles that are already in valgus (outward position), using either a straight or valgus bent nail makes aligning the ankle fusion straight very hard. The connection between the nail 30 and nail adapter 32 can only be applied with the nail 30 in its original valgus (outward) bent. If the nail 30 is flipped (i.e., rotated) to help with the reduction (by converting the nail to "varus" or "inward" position to correct the outward deformity of the ankle), the nail adapter 32 also must be flipped as there is only one "correct" method to connect the nail 30 with the nail adapter 32. Flipping the aiming arm 20 will result in changing the position and direction of the locking screws. This makes insertion of the locking screws difficult to impossible and carries a risk to the soft tissues or nerves.

As can be seen, there is a need for a nail and nail adapter system that avoids valgus (outward) malreduction in cases of ankle fusion (arthrodesis) surgery, especially for ankles which are already deformed in valgus (outward) position.

SUMMARY OF THE INVENTION

The present invention provides a nail and a nail adapter system with multiple possible connection positions therebetween. The inventive system helps to avoid valgus (outward) malreduction in cases of ankle fusion (arthrodesis) surgery, especially for ankles which are already deformed in valgus (outward) position.

In one aspect of the present invention, an arthrodesis nail and nail adapter system having a plurality of coupling positions is provided, comprising: a bent arthrodesis nail having a plurality of evenly spaced notches and a nail adapter having a plurality of evenly spaced protrusions corresponding to the evenly spaced plurality of notches.

In another aspect of the present invention, an arthrodesis nail adapter and target arm system having a plurality of coupling positions is provided, comprising: a nail adapter having a predetermined coupling orientation with a bent arthrodesis nail and a target arm having a plurality of coupling positions with the nail adapter.

These and other features, aspects and advantages of the present invention will become better understood with reference to the following drawings, description, and claims.

DETAILED DESCRIPTION OF THE INVENTION

Figures 1A, 1B, 1C:
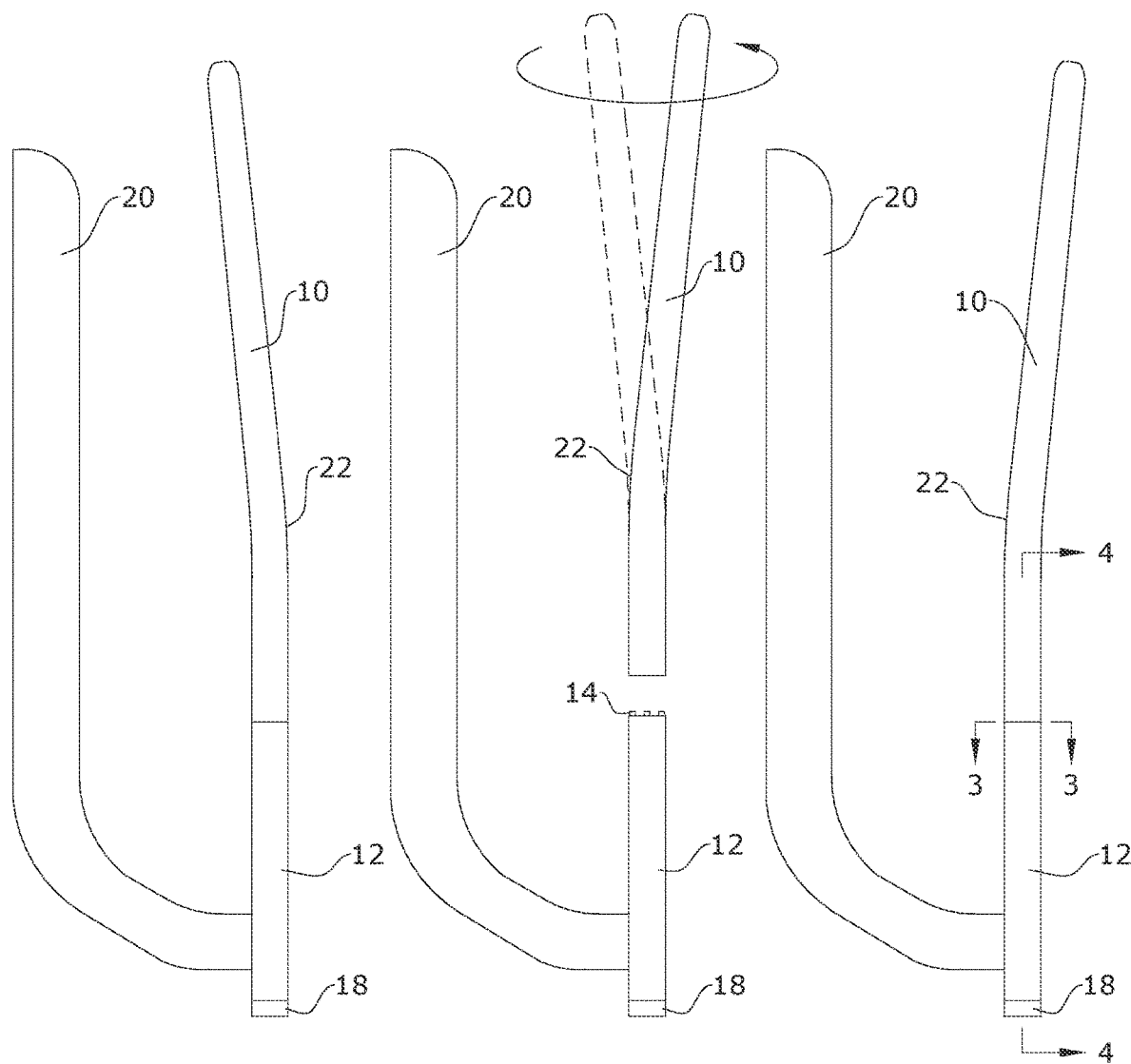
FIG. 1A is a front view of a nail and nail adapter according to an embodiment of the present invention.
FIG. 1B is a front view thereof, shown rotating the nail.
FIG. 1C is a front view thereof, shown with the nail rotated.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, one embodiment of the present invention is a bent arthrodesis nail, such as a tibiotalocalcaneal (TTC) nail, and an arthrodesis nail adapter configured for better correction of the position of the ankle in ankle fusion (arthrodesis) surgery. The inventive TTC nail enables the slots (notches) and teeth (prongs) to be connected in more than one fixed direction.

As used herein, the term "flip" referring to the position of a nail means to rotate the nail around the longitudinal axis.

The present invention enables multiple possible connection or coupling positions between the nail and the nail adapter. If a surgeon flips the nail to get better reduction, he or she may connect to the nail adapter in that flipped position without flipping the nail adapter and without effect on the aiming targeting device (used to guide insertion of locking screws that stabilize the nail in the bone). This provides a major advantage in correction of valgus ankle deformity or mal-position as flipping the nail will automatically use the valgus bent as a varus bent (after rotating the nail) in the TTC to correct the valgus deformity.

The surgeon may also, for example, turn the nail 90 degrees (in either direction) to use the nail bend as a tool to correct apex anterior or apex posterior deformity. A ¼ or ½ turn by the surgeon to correct corresponding deformities in the ankle position for the proposed fusion without having to flip the nail adapter allows use of the aiming device in insertion of the locking screws.

The nail (with the notches in its distal part) may rotate in the ankle and be flipped and the notches may still be fitted to the nail adapter teeth in the new rotation without having to flip the nail adapter (connector). Keeping the nail adapter in its original position enables the target arm to remain in a predetermined safe position for applying locking screws to secure the nail to the bone.

For example, if the nail has four evenly spaced notches and the nail connector has four mated evenly spaced protrusions, the nail may be coupled to the nail connector in a position selected from the group consisting of 0° (with the bent aiming lateral), 90° (with the bent anterior), 180° (with the bent medial to correct valgus mal position), and 270° (with the bent posterior) rotation from a predetermined initial position. This enables correction of valgus ankle and may be used for other deformities as well, such as forward and backward flexion.

This same technique may be used in nails used for other purposes. For example, some embodiments of the present invention may include a flexible connection tibial nail (used for tibia fracture), a flexible connection femoral nail (ante grade and retro grade), and/or a flexible connection humeral nail. If the surgeon applies the nail and finds the fracture is flexed, the surgeon may flip the nail to correct the deformity and still use the targeting device to apply the locking screws. This may be through the nail-nail adapter connection or through the nail adapter-target arm connection.

In some embodiments, the aiming device may be modified to accommodate alternate connection orientations with the nail connector, providing an inventive arthrodesis nail adapter and target arm system. The nail and nail connector may have a single connection orientation. When flipping the nail, the nail adapter may flip with it. The aiming target may be flipped with respect to the adapter (connector) such that the aiming target remains in a preferred position with respect to the subject's ankle as in the neutral position.

Referring to FIGS. 1A, 1B, 1C, 2A, 2B, 2C, and 3-7, FIG. 1A shows a nail 10 having a valgus bend 22 coupled to a nail adapter 12 according to an embodiment of the invention. An aiming device 20 or target arm extends perpendicularly from the nail adapter 12 and curves to an orientation parallel to the nail adapter 12.

Figures 2A, 2B, 2C, 3:
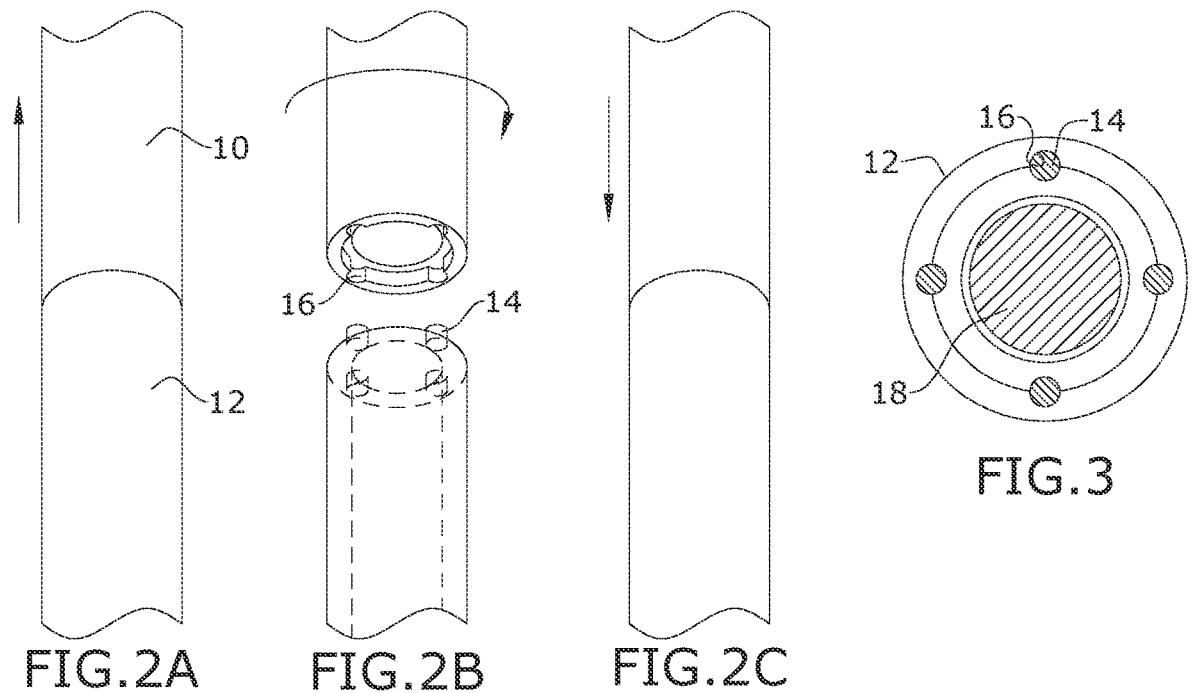
FIG. 2A is a detail view thereof.
FIG. 2B is a detail view, shown rotating the nail.
FIG. 2C is a detailed view thereof, shown with protrusions and notches reengaged.
FIG. 3 is a sectional view thereof, taken along line 3-3 of FIG. 1C.

As shown in FIGS. 1B and 2B, the nail 10, having a plurality of slots or notches 16, may be multi-directionally coupled to a plurality of prongs or protrusions 14 extending from the nail adapter 12. For example, the nail may be rotated 180° and coupled to the nail adapter 12, as FIGS. 1C, 2A, 2B, and 2C show. While FIGS. 2B and 2C illustrate four protrusions 14 corresponding to four notches 16, the invention is not limited to a particular number, provided that the nail 10 may be coupled to the nail adapter 12 in multiple positions.

Figure 4:
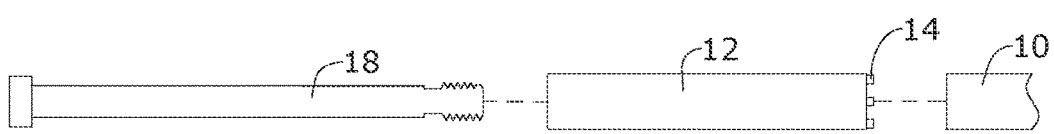
FIG. 4 is an exploded view thereof.
Figure 5:
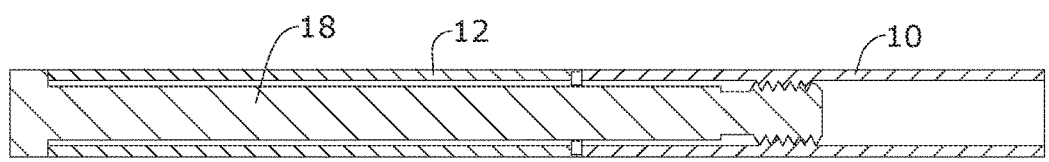
FIG. 5 is a sectional view thereof, taken along line 4-4 of FIG. 1C.
Figure 6:
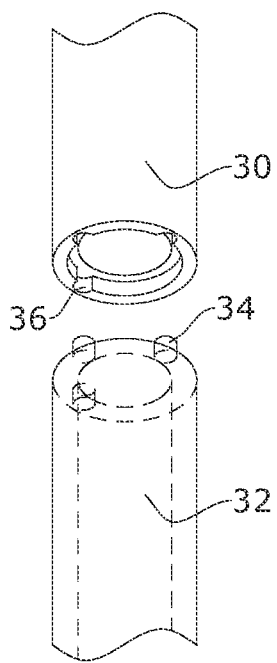
FIG. 6 is a detail perspective view of a prior art device.
Figure 7:
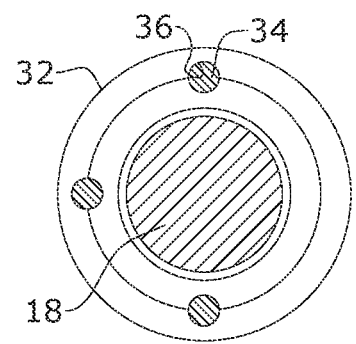
FIG. 7 is a sectional view thereof.

The nail 10 may be removably fixed in place on the adapter 12 using a nail connection or nail adapter screw 18. As shown in FIGS. 4 and 5, the screw 18 passes axially through the nail adapter 12 into the nail 10 and is rotated such that the nail 10 is fastened onto threads on the screw 18.

In comparison, prior art nails 30 have notches 36 that couple with protrusions 34 on the nail adapter 32 in only a single orientation. See FIGS. 6-7.

In an alternate embodiment, an arthrodesis nail adapter and target arm system have a plurality of coupling positions, comprising: a nail adapter having a predetermined coupling orientation with a bent arthrodesis nail and a target arm having a plurality of coupling positions with the nail adapter.

It should be understood, of course, that the foregoing relates to exemplary embodiments of the invention and that modifications may be made without departing from the spirit and scope of the invention as set forth in the following claims.

What is claimed is:

1. An arthrodesis nail and nail adapter system having a plurality of coupling positions, comprising:
    a unitary bent arthrodesis nail having a longitudinal axis of rotation, a first end orthogonal thereto with a plurality of evenly spaced notches, and a second end extending from a bend therein at a fixed angle; and
    a nail adapter having a plurality of evenly spaced protrusions extending longitudinally from a first nail adapter end corresponding mateably to the plurality of evenly spaced notches throughout the plurality of coupling positions;
    wherein the plurality of coupling positions are positions of the nail adapter relative to the unitary bent arthrodesis nail; and wherein the nail adapter is operative to remain in an original position when the unitary bent arthrodesis nail is rotated around its longitudinal axis.

2. The arthrodesis nail and nail adapter system of claim 1, wherein the nail adapter is effective to couple coaxially with the first end of the unitary bent arthrodesis nail at a 90°, a 180°, and a 270° rotation from a first of the plurality of coupling positions.

3. The arthrodesis nail and nail adapter system of claim 1, further comprising an aiming device, wherein the aiming device mates with the nail adapter in a single predetermined position throughout the plurality of coupling positions.

4. The arthrodesis nail and nail adapter system of claim 1, further comprising a nail adapter screw effective to removably fasten the unitary bent arthrodesis nail to the nail adapter.

5. The arthrodesis nail and nail adapter system of claim 1, wherein the unitary bent arthrodesis nail is selected from the group consisting of: a tibiotalocalcaneal nail, a tibial nail, a femoral nail, and a humeral nail.

6. The arthrodesis nail and nail adapter system of claim 1, further comprising at least one locking screw effective to fasten the unitary bent arthrodesis nail to a bone.

7. The arthrodesis nail and nail adapter system of claim 1, further comprising an aiming device and a nail adapter screw effective to removably fasten the unitary bent arthrodesis nail to the nail adapter, wherein the first end of the unitary bent arthrodesis nail and the nail adapter are effective to couple coaxially in 90°, a 180°, and a 270° rotation relative to each other from a first of the plurality of coupling positions.

8. The arthrodesis nail and nail adapter system of claim 1, wherein the nail adapter is operative to couple a target arm in a single predetermined position relative to a bone with the unitary bent arthrodesis nail when the unitary bent arthrodesis nail is in a lateral position, an anterior position, a medial position and a posterior position relative to the bone.

9. The arthrodesis nail and nail adapter system of claim 1, wherein the arthrodesis nail is a tibiotalocalcaneal nail.

10. An arthrodesis nail adapter and target arm system, comprising:
    a unitary bent arthrodesis nail extending along a longitudinal axis from a first end to a fixed angle bend and from the fixed angle bend to a second end;
    a nail adapter mated to the first end of the unitary bent arthrodesis nail; and
    a target arm having a plurality of coupling positions with the nail adapter;
    wherein the nail adapter is operative to keep the target arm in an initial position relative to a subject's ankle when the unitary bent arthrodesis nail is rotated around its longitudinal axis within the subject's ankle.

* * * * *